United States Patent [19]
Esser

[11] Patent Number: 6,099,827
[45] Date of Patent: Aug. 8, 2000

[54] ANTIPERSPIRANT OR DEODORANT COMPOSITIONS

[75] Inventor: Isabelle Claire Helen Marie Esser, Port Sunlight, United Kingdom

[73] Assignee: Helene Curtis, Inc., Chicago, Ill.

[21] Appl. No.: 08/991,454

[22] Filed: Dec. 16, 1997

[30] Foreign Application Priority Data

Dec. 23, 1996 [GB] United Kingdom .................. 9626794

[51] Int. Cl.⁷ ............................... A61K 7/32; A61K 7/00
[52] U.S. Cl. ............................ 424/65; 424/400; 424/401
[58] Field of Search ............................... 424/68, 400, 401

[56] References Cited

U.S. PATENT DOCUMENTS 4,745,186  5/1988  Mudd et al. ............................ 536/119

FOREIGN PATENT DOCUMENTS 595339    5/1994  European Pat. Off. .
1409533   8/1975  United Kingdom .
96/04884  2/1996  WIPO .

OTHER PUBLICATIONS

International Search Report Application No. PCT/EP 97/06958 dated May 12, 1998.

*Primary Examiner*—Shelley A. Dodson
*Attorney, Agent, or Firm*—Matthew Boxer

[57] ABSTRACT

An antiperspirant or deodorant cosmetic aerosol composition suitable for topical application to the human skin, comprising:
  i. from 5 to 30% of an antiperspirant or deodorant active;
  ii. from 1 to 50% of a moisturising cream; and optionally
  iii. a carrier for the antiperspirant or deodorant active.

11 Claims, No Drawings

ANTIPERSPIRANT OR DEODORANT COMPOSITIONS

The invention relates to antiperspirant or deodorant aerosol compositions, but in particular to antiperspirant aerosol compositions, comprising a moisturising cream suitable for topical application to human skin.

The deodorant and antiperspirant market is dominated with products based on aluminium or zirconium salts which are intended to prevent, or at least control, perspiration at the skin surface, particularly on the underarm, whilst often simultaneously providing a perceived degree of deodorancy.

A principal disadvantage of many deodorants and antiperspirants is their perceived skin unfriendliness. More particularly, the presence of volatile carriers such as volatile silicones and ethanol, and indeed deodorant and antiperspirant actives is perceived to have a drying and tightening effect on a user's skin following application, resulting in dry skin, reduced skin elasticity and an unpleasant skin sensation.

Many deodorants and antiperspirants can also result in a stinging sensation on the skin following application due to the presence of astringent, skin drying materials such as ethanol. Stinging is a particularly problematic when a deodorant or antiperspirant is applied following shaving.

The above disadvantages deter many consumers from utilising deodorants and antiperspirants thereby depriving the consumer of the benefits to be derived from such cosmetics.

An object of the invention is to provide such a composition which has excellent antiperspirant or deodorant efficacy, excellent cosmetic properties and aesthetics such as comfort in use, smoothness on application, and non-skin drying. The moisturising cream in the composition may also provide moisturising effect.

A further object of the invention is to provide a deodorant or antiperspirant composition which also exhibits reduced stinging upon application, and has low irritation potential.

According to the invention there is provided an antiperspirant or deodorant cosmetic aerosol composition suitable for topical application to the human skin, comprising an antiperspirant or deodorant active, and a moisturising cream.

Preferably, the antiperspirant active comprises 5–25% by weight of the composition. Normally the antiperspirant or deodorant composition will additionally comprise a carrier for the antiperspirant or deodorant active and a non-polar hydrocarbon propellant composition.

In a preferred embodiment, the composition does not contain short chain monohydric alcohols, in particular ethanol, which may be responsible for stinging of the antiperspirant or deodorant compositions, as well as contributing to the drying of the skin.

Advantageously, the composition comprises non-volatile emollients.

In a preferred embodiment the invention provides an antiperspirant or deodorant aerosol composition suitable for topical application to the human skin, comprising:

i. 5–30% by weight of the total composition of an antiperspirant or deodorant active;

ii. 0.1 to 50% (more preferably 5 to 30%) by weight of a moisturising cream; and iii. 20 to 90% non-polar hydrocarbon propellant composition.

The moisturising cream component of the compositions according to the invention may comprise an hygroscopic material known as humectant, which may be preferably a polyol or an alcohol, and may be present at a level of 0.1 to 50%, preferably 1 to 30%, most preferably 1.5 to 10% by weight of the total composition.

Advantageously the moisturising cream comprises a humectant. Humectants are well know in the art, and are cosmetic ingredients intended to increase the water content of the top layers of the skin. This group of ingredients includes primarily hygroscopic agents employed for this specific purpose. Humectants of particular interest for the present invention are polyols and alcohols such as sorbitol, glycerol, ethylene glycol , propylene glycol or mixtures thereof. Preferably, the humectant contains a hydroxyl group.

Surprisingly, we have found that a moisturising cream can be incorporated into an antiperspirant or deodorant cosmetic composition to produce an antiperspirant or deodorant composition which has improved and attractive cosmetic characteristics expected of such compositions as well as excellent efficacy, low irritation potential and non-stinging upon application.

Therefore, the invention provides an antiperspirant or deodorant compositions which exhibit excellent wetness or odour control, but simultaneously contain a cream which moisturises the stratum corneum.

Preferably, the moisturising cream in the compositions according to the invention can be a solid or a semi-solid emulsion, although the term can equally be applied to non-aqueous products such as wax-solvent based products and ointments. The term also includes dispersion products of cream consistency.

Moisturising creams used in the compositions according to the invention are those which aid retention of water to plasticise outer layers of the epidermis to promote soft, smooth skin. If water is lost more rapidly from the stratum corneum that it is received from the lower layers of the epidermis, the skin becomes dehydrated and loses its flexibility.

Moisturising creams used in compositions according to the invention may typically work by one or a combination of three main routes, namely occlusion, humectancy and restoration of deficient materials. A given moisturising cream may act by any number of these three preferred routes.

Occlusion consists of reducing the rate of transepidermal water loss through old or damaged skin or in protecting otherwise healthy skin from the effect of a drying environment. The second approach is to use humectants to attract water from the surrounding environment, thereby supplementing the skin's water content. The third approach is to determine the mechanism of the skin moisturisation process, and supplement the skin in its deficiencies.

In compositions according to the invention, it is the moisturising cream component of the composition which provides a moisturising benefit.

The composition according to the invention comprises an antiperspirant active suitable for use in aerosol formulations. Examples of suitable actives include aluminium salts, aluminium complexes, for example aluminium halides, aluminium hydroxy halides, and mixtures thereof. Other generally used actives will be known to those skilled in the art. Preferred actives include AACH (Activated Aluminium chlorohydrate).

The amount of antiperspirant active present in the composition according to the invention is from 5 to 30%, most preferably 5 to 25% of the total composition.

The deodorant active used in the cosmetics of the invention can be any deodorant active known in the art such as alcohols with the exception of ethanol, antimicrobial actives such as polyhexamethylene biguanides, non-microbiocidal deodorant actives such as triethylcitrate, bactericides and bacteriostatis.

The carrier material for the antiperspirant composition according to the invention can also comprise one or more volatile carrier fluids, one or more non-volatile emollients, and one or a combination of thickener and/or structurant materials if required.

The carrier fluid is selected according to the physical form of the cosmetic composition, e.g. volatile low viscosity silicones, low molecular weight hydrocarbons, alcohols with the exception of ethanol and can be selected by those skilled in the art to provide appropriate physical and sensory properties for the product.

The emollient, if used in the composition, may consist of a single emollient compound or a mixture of emollients, and can typically include fatty acids and fatty alcohol esters, slightly water soluble ethers and alcohols, hydrocarbons, water insoluble ethers, mineral oils and polyorganosiloxanes, and mixtures thereof.

The thickening or structurant agent, when required, is selected according to the product form of the cosmetic composition. It can be any of a number of compositions, including, for example, hydrogenated vegetable oil, hydrogenated castor oil, fatty acids, beeswax, paraffin wax, silicone was, fatty alcohols, polymers such as hydroxypropylcellulose, clays such as Bentone, natural or synthetic gums, or mixtures or combinations thereof.

The composition according to the invention can optionally comprise other ingredients commonly used in antiperspirant or deodorant aerosol formulations, in addition to those already identified.

For example surfactants, fillers, fragrances, preservatives and colouring agents for example. These ingredients are selected according to the physical and chemical from of the cosmetic composition.

Surfactants can comprise optionally up to 25% and preferably less than 8% of the total product.

Fillers can comprise up to about 10% of the total product and are normally less costly that the essential components of the invention, thereby reducing overall cost. Suitable fillers include aluminium stearate, aluminium tri-stearate, calcium stearate, talc or finely divided polyethylene, an example of which is ACUMIST B18.

Fragrances typically comprise up to about 1% of the total product.

Colouring agents and preservatives can be added as desired.

The ingredients which can optionally be present in the carrier can conveniently form the balance of the composition.

The composition according to the invention can take any form of a product suited to or adapted for topical application to human skin, and is usually contained in a suitable holder or dispenser to enable it to be applied to the area of the skin, particularly the underarm, where control of perspiration and deodorancy is required.

EXAMPLES

Antiperspirant compositions according to the invention have been prepared using methods of manufacturing known in the art.

The invention is further illustrated by the following example.

Example 1

The following 2 antiperspirant aerosol compositions was formulated using methods well known in the art.

| Material | % |
|---|---|
| AACH | 5.0000 |
| Volatile silicone Q2 1465 | 6.3737 |
| Bentone 38 | 0.3900 |
| Fragrance | 0.7000 |
| Fluid AP | 0.3705 |
| Octyldodecanol | 0.1170 |
| Aerosil 200 | 0.0488 |
| CAP 40 | 87.000 |
| Total | 100.00 |

| INCI NAME | AP INGREDIENT | MOISTURISING CREAM | TOTAL BASE | TOTAL PRODUCT |
|---|---|---|---|---|
| Aluminium Chlorohydrate | 40.161 | — | 40.161 | 10.000 |
| Cyclomethicone | 30.012 | 19.000 | 49.012 | 12.204 |
| Quaternium-18-Hectorite | 2.016 | 2.000 | 4.016 | 1.000 |
| PPG-14 Butyl Ether | — | 2.850 | 2.850 | 0.710 |
| Octyldodecanol | — | 0.900 | 0.900 | 0.224 |
| Silica | — | 0.250 | 0.250 | 0.062 |
| Parfum | 2.811 | — | 2.811 | 0.7000 |
| Butane/Isobutane/Propane | — | — | — | 75.100 |
| | 75.00 | 25.00 | 100.00 | 100.00 |

What is claimed is:

1. A non-skin drying antiperspirant or deodorant composition suitable for topical application to the human skin, comprising:
    (i) 5 to 30% by weight of the total composition of an antiperspirant or deodorant active;
    (ii) 0.1 to 50% by weight of a moisturizing cream;
    (iii) 20 to 90% non-polar hydrocarbon propellant composition;
wherein said moisturizing cream comprises a humectant and a non-volatile emollient.

2. An antiperspirant composition according to claim 1, wherein the composition is free of any short chain monohydric alcohol.

3. An antiperspirant composition acco rding to claim 2, wherein the short chain monohydric alcohol is ethanol.

4. An antiperspirant composition accor ding to claim 1, wherein the moisturising cream comprises 2 to 100% of a humectant.

5. An antiperspirant composition according to claim 4, wherein t he humectant is sorbitol, glycerol, ethylene glycol, propylene glycol, or mixtures thereof.

6. An antiperspirant composition according to claim 1, wherein the moisturising cream is a solid or semi-solid emulsion.

7. An antiperspirant composition according to claim 1, additionally comprising a volatile carrier.

8. An antiperspirant composition according to claim 1, additionally comprising a non-volatile emollient.

9. An antiperspirant composition according to claim 8, wherein the non-volatile emollient is selected from the group consisting of fatty acids or fatty alcohol esters, slightly water soluble ethers or alcohols, hydrocarbons, water insoluble ethers, mineral oils and polyorganosiloxanes, and mixtures thereof.

10. An antiperspirant composition according to claim 1, additionally comprising a structurant.

11. An antiperspirant composition according to claim 10, wherein said structurant is selected from the group consisting of hydrogenated vegetable oil, hydrogenated castor oil, fatty acids, beeswax, paraffin wax, silicone wax, fatty alcohols, polymers, clays, natural gums, synthetic gums and mixtures thereof.

* * * * *